United States Patent
Dortmans et al.

(10) Patent No.: US 7,387,761 B2
(45) Date of Patent: Jun. 17, 2008

(54) METHOD FOR MANUFACTURING A GLASS INFILTRATED METAL OXIDE INFRASTRUCTURE

(75) Inventors: Leonardus Johannes Dortmans, Helmond (NL); Gijsbertus de With, Valkenswaard (NL); Qingshan Zhu, Eindhoven (NL)

(73) Assignee: Nederlandse Organisatie Voor Toegepast-Natuurwetenschappelijk Onderzoek TNO, Eindhoven (NL)

( * ) Notice: Subject to any disclaimer, the term of this patent is extended or adjusted under 35 U.S.C. 154(b) by 329 days.

(21) Appl. No.: 10/507,894

(22) PCT Filed: Mar. 28, 2003

(86) PCT No.: PCT/NL03/00236

§ 371 (c)(1),
(2), (4) Date: Sep. 17, 2004

(87) PCT Pub. No.: WO03/082219

PCT Pub. Date: Oct. 9, 2003

(65) Prior Publication Data

US 2005/0181217 A1 Aug. 18, 2005

(30) Foreign Application Priority Data

Mar. 28, 2002 (EP) ................................. 02076220

(51) Int. Cl.
*C05B 35/64* (2006.01)
(52) U.S. Cl. ...................................... 264/642; 264/676
(58) Field of Classification Search .................. None
See application file for complete search history.

(56) References Cited

U.S. PATENT DOCUMENTS

| | | | |
|---|---|---|---|
| 4,455,284 A | 6/1984 | Sizyakov et al. | |
| 4,772,436 A | 9/1988 | Tyszblat | |
| 5,045,508 A | 9/1991 | Brow et al. | |
| 5,447,967 A | 9/1995 | Tyszblat | |
| 5,695,337 A * | 12/1997 | Tyszblat Sadoun | ......... 433/213 |

FOREIGN PATENT DOCUMENTS

| | | |
|---|---|---|
| DE | 4020 598 | 1/1991 |
| DE | 198 52 740 | 5/2000 |
| WO | 94/04092 | 3/1994 |

OTHER PUBLICATIONS

Chemical Abstract, American Chemical Society, XP 000286593, 115(1991) Sep. 9, No. 10, Columbus, Ohio, US, Kishikawa et al, "Manufacture of fusion-bonded glass-pottery articles".

* cited by examiner

*Primary Examiner*—Jennifer McNeil
*Assistant Examiner*—Timothy M. Speer
(74) *Attorney, Agent, or Firm*—Nixon & Vanderhye P.C.

(57) ABSTRACT

The invention relates to a method for manufacturing a composite of a porous metal oxide infrastructure and a glass infiltrated in the pores of the infrastructure, wherein the method comprises at least the following steps: providing a glass which is suitable for infiltration and compatible with the metal oxide infrastructure; heating the glass in a nitrogen rich environment; and infiltrating the metal oxide infrastructure with the glass. The invention also relates to a method for avoiding or reducing stress corrosion in a glass infiltrated metal oxide infrastructure, comprising heating a glass composition under a nitrogen gas atmosphere before infiltrating the metal oxide infrastructure. The invention further relates to a glass infiltrated metaloxide infrastructure obtainable by any of these methods.

17 Claims, 1 Drawing Sheet

Slow crack growth behavior of $Al_2O_3$-oxynitride glass composite

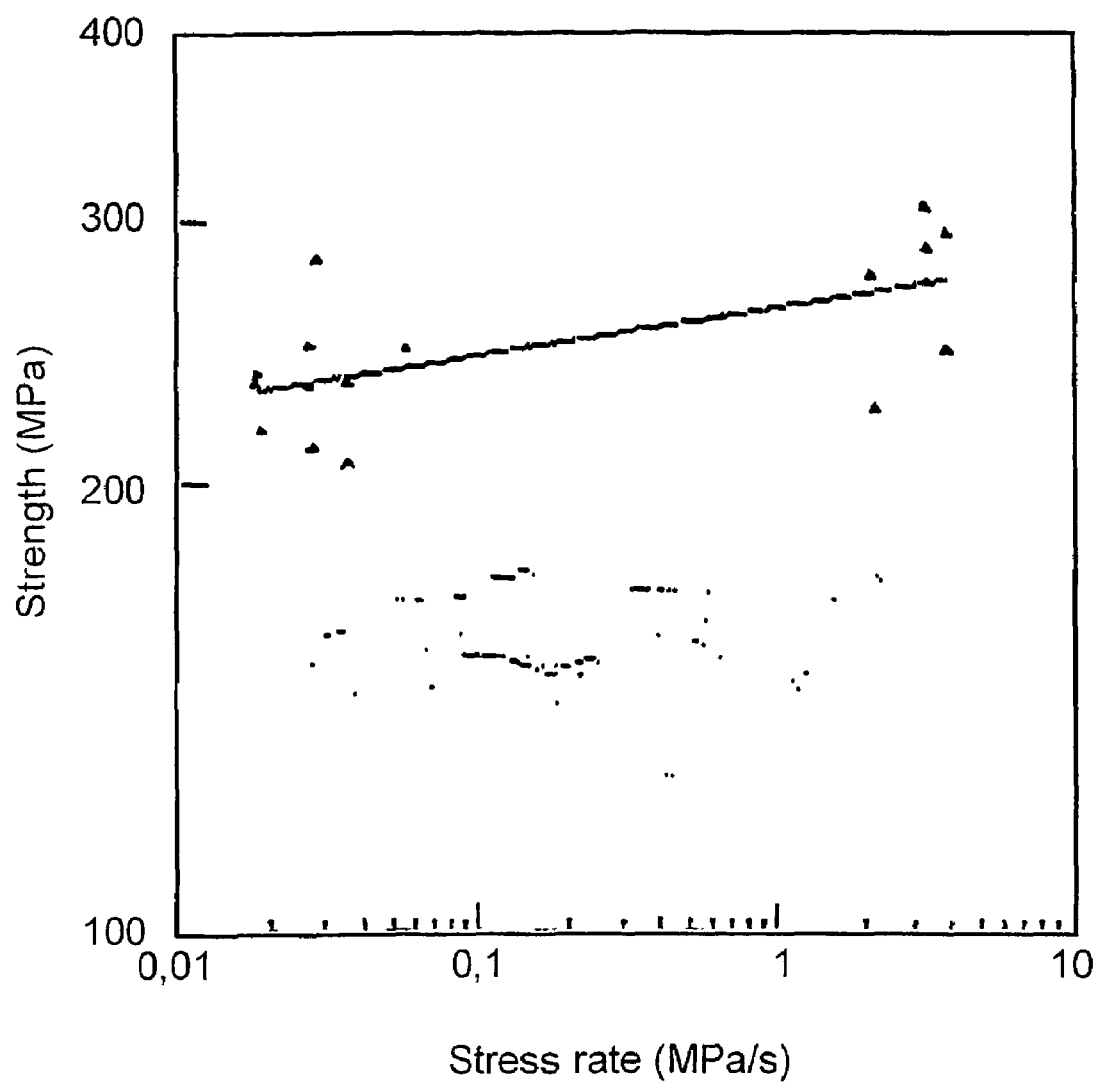
Fig. 1 Slow crack growth behavior of $Al_2O_3$-oxynitride glass composite

METHOD FOR MANUFACTURING A GLASS INFILTRATED METAL OXIDE INFRASTRUCTURE

This application is the U.S. national phase of international application PCT/NL03/00236 filed 28 Mar. 2003 which designated the U.S. and claims benefit of EP 02076220.9, dated 28 Mar. 2002, the entire content of which is hereby incorporated by reference.

The invention is related to a method for manufacturing a composite of a metal oxide infrastructure and a glass infiltrated in the pores of the infrastructure to a method for avoiding or reducing stress corrosion in a glass infiltrated metal oxide infrastructure and a glass infiltrated metal oxide structure. Said composite is for instance useful in the field of dental prothesis.

U.S. Pat. No. 4,772,436 discloses a method for manufacturing such a composite as a ceramic dental prosthesis. This method comprises infiltration at elevated temperatures of a glass in an infrastructure which has been obtained by binding metal oxide particles in a predetermined shape, often the shape of a tooth or a part thereof. This shape is obtained from a model produced in a moulding mass, such as plaster, which exhibits slight linear expansion during solidification. A method of producing an infrastructure in its predetermined shape involves, as described in more detail, preparation of a slip comprising a suspension in water of metal oxide particles such as aluminium oxide and/or zirconia, to which is added a suspension stabilization agent and optionally a pH control agent. The slip is then poured into the molding mass so that the metal oxide particles aggregate. The model with the slip is then baked in order to effect initial dehydration of the model of the tooth which causes its withdrawal. The solid phase of the metal oxide particles is then slightly fritted providing the infrastructure. Usually the metal oxide infrastructure comprises alumina, but may also include magnesium oxide, lanthanum oxide or a rare earth metal oxide. Optionally zirconium oxide particles are used in admixtures in amounts that can be significant. Zirconium oxide may also, in pure form or stabilised with yttrium oxide, be employed to construct the infrastructure.

The infiltration is carried out by placing a glass and the infrastructure in contact with each other and raising the temperature to the infiltration temperature which usually lies within a range from 1000 to 1400° C. The infiltration characteristics are further depending on, amongst others, the heating rate and the time during which the elevated temperature is maintained. The glass preferably exhibits, at the infiltration temperature, characteristics which enable easy wetting of the metal oxide infrastructure, meaning that surface energy of the glass, at the infiltration temperature, must preferably be lower than the surface energy of the infrastructure. The wetting characteristics can be increased by introducing, for instance, lead oxide, boron oxide or vanadium oxide. The reactivity of the glass with regard to the metal oxide must be neither too strong, nor too weak. This is obtained by using a glass which contains initially metal oxides such as alumina and/or zirconia in an amount that is slightly lower than, but close to, the saturation of the glass vis-à-vis those metal oxides at the infiltration temperature. The infiltration temperature can be raised if small amounts of magnesium oxide powder and/or zirconium oxide powders are added to the glass. Also lanthanum oxide or powders of yttrium oxide or rare earth oxides allow for raising the infiltration temperature.

Dental prostheses made of glass infiltrated metal oxide infrastructures are, in use, as a result of for instance chewing, subjected to (cyclic) loading, leading to a phenomenon usually referred to as fatigue. Due to exposure to these conditions, a dental prosthesis, or a part thereof, will ultimately break. The fracture is understood to be a result of slow crack growth of presumably small defects present or flaws in the composite. This slow crack growth may also be referred to as Subcritical Crack Growth (SCG). It is believed that crack growth of these defects or flaws occurs on a microscopic scale by a process of slow diffusion which is enhanced by repeatedly applying stress to the prosthesis and this particular fatigue related wear phenomenon is therefor also referred to as stress corrosion. Due to a process of slow crack growth which results in fracture, the dental prosthesis has a limited lifetime after placement within the set of teeth of a patient.

It is an object of the invention to provide a method for manufacturing a composite of a metal oxide infrastructure and a glass infiltrated in pores of the infrastructure and, to obtain a composite with a higher resistance against slow crack growth compared to composites obtained by methods of manufacturing from the prior art.

The present inventors have found that this aim is reached by applying an extra processing step before infiltration of the glass in the infrastructure.

More in detail, the present invention relates to a method for manufacturing a composite of a porous metal oxide infrastructure and a glass infiltrated in the pores of the infrastructure, wherein the method comprises the following steps:

providing a glass which is suitable for infiltration and compatible with the metal oxide infrastructure; heating of the glass in a nitrogen rich gas environment; and infiltrating the metal oxide infrastructure with the glass.

In a second aspect, the present invention relates to a method for avoiding or reducing stress corrosion in a glass infiltrated metal oxide infrastructure, comprising heating a glass composition under a nitrogen gas atmosphere before infiltrating the metal oxide infrastructure.

In yet a further aspect, the present invention relates to the glass is filtrated metal oxide structures obtainable by the methods of the invention.

Without wishing to be bound by any theory, it is believed that as a result of the heat treatment the glass has become nitrided, at least to a certain degree. The composite obtained by applying the method of the present invention has been found to exhibit superior mechanical properties. Therefore in a further aspect, the present invention also relates to the glass infiltrated metal oxide infrastructure obtainable by the process of the invention. Most particularly, the so-called slow or Subcritical Crack Growth (SCG) exponent n, becomes higher than the SCG exponent n of the corresponding glass infiltrated metal oxide infrastructure that has not been subjected to heating in a reactive nitrogen rich gas atmosphere according to the invention. The SCG exponent n is experimentally obtained on the basis of a number of experiments in which the fracture strength is determined as a function of the stress rate. By plotting the fracture strength (in MPa) as a function of the logarithm of the stress rate (in MPa/s) and drawing a straight line through the data applying the least squares method, the slope of the line equals: $1/(n+1)$. As can be seen from the working example herein below the SCG exponent n can have values of up to and even above 30. Higher values of n implicate a higher resistance against subcritical crack growth, which means that the composite can sustain for a much longer period of time cyclic loading such a composite is subjected to during its intended use, or alternatively, the composite can have the same mechanical properties while using less volume of material than when using the glass composition not treated in accordance with the present invention. This allows for the fabrication of finer or thinner features on the structures.

In a more preferred embodiment of the method of the present invention the heating is carried out under a nitrogen-rich gas atmosphere. The nitrogen-rich gas atmosphere may for instance comprise a reactive gas environment containing nitrogen, nitrogen and hydrogen, or ammonia and hydrogen. Preferably, the nitrogen containing compound in the gas environment is present in an amount of at least 80 wt. %, and more preferably at least 90 wt. %. In the most preferred embodiment, the gas atmosphere consists essentially of nitrogen gas.

Preferably, the heating step is carried out at a temperature in a range from 1200° C. to 1600° C. for preferably at least 4 up to 16 hours. Preferably, the heating is carried out for 6 up to 10 hours. Even more preferred, the heating step in the methods of the invention is carried out for about 8 hours.

The preferred conditions allow for optimising within a parameter window provided by the time, temperature, gas mixture, and desired levels of nitrogen substitutionally incorporated in the glass. These method parameters may be set in accordance with the desired improvements in the SCG exponent n and the preferred lifetime and/or the fine geometry of the glass infiltrated metal oxide infrastructure.

The heat treated glass may be crushed before infiltrating the metal oxide infrastructure. This allows for faster infiltration in the pores of the metal oxide structure.

In the methods of the present invention the glass used has preferably a surface energy at said infrastructure which is, at the infiltration temperature, lower than the surface energy of the infrastructure.

The metal oxide infrastructure used in the method of the present invention can in fact be made of any metal oxide material suitable to be infiltrated by glass. Preferably, the metal oxide infrastructure comprises a structure selected from the group consisting of alumina, zirconia, zirconia toughened alumina, magnesium, magnesium and/or aluminum spinels and hydroxyapatite.

Especially good results are obtained when said structure to be infiltrated is comprises of alumina. The balance between 80 and 99.9 wt. % can be any material compatible with the main material and suitable for the intended use. If prostheses are to be made, of course, all ingredients of the infrastructure must be biocompatible.

Examples of suitable other metal compounds that may be present in the metal oxide structure to be infiltrated are zirconium oxide, preferably up to an amount of 20 wt. %; and magnesium oxide, preferably up to 4 wt. %.

The glasses which can be used in the methods of the present invention are all glasses which are already known to be useful for glass infiltration.

Very suitable, however, are glasses which comprise metal oxides which are employed in the infrastructure to be infiltrated, wherein each metal oxide preferably is present in a slightly less amount than at a saturation of the glass relative to that metal oxide at the infiltration temperature. This makes that the glass and metal oxide used do not aggressively influence each other's composition.

Preferably, the metal oxides in the glass encompass aluminum oxide.

Preferred glasses comprise alumina in an amount between 12 and 23 wt. %, calcium oxide in an amount of 1 to 26 wt. %, the balance being silica, and optionally other metal oxides, colouring agents and processing aids. Suitable other metal oxides are $B_2O_3$ that may be present in an amount up to 30 wt. %, and preferably between 10 and 25 wt. %; $La_2O_3$ that may be present in an amount of up to 45 wt. %, preferably in an amount between 25 and 40 wt. %; titanium oxide that may be present in an amount of up to 8 wt. %, and rare earth metal oxides.

Another suitable constituent in the glass composition is an oxide, preferably selected from the group consisting of lead oxide, boron oxide or vanadium oxide, in an amount sufficient to increase the wettability of the glass. Generally amounts of maximally 5 wt. %, preferably 2 wt. % and most preferable maximally 1 wt. % are suitable for this aim.

Further, the glass can contain conventional colour-imparting metal oxide, generally in an amount of up to 3 wt. % drawn to the glass composition.

When the metal oxide infrastructure to be infiltrated is comprised of or contains hydroxyapatite in an amount of more than 60 wt. %, the glass to be infiltrated preferably comprises 20-30 wt. % $B_2O_3$; 10-25 wt. % $Li_2O$ and silica as the balance, optionally with up to 6 wt. % CaO.

In a sophisticated embodiment of a method according to the invention the infiltration is carried out under a nitrogen-rich gas atmosphere. This prevents the nitrogen oxygen exchange as taken place during the heat treatment to be reversed during the infiltration.

In an extended embodiment, providing the glass comprises intimately mixing oxides and carbonates, e.g. by wet ball milling in alcohol, followed by drying the mixture in an oven. This has the advantages that the different types of oxides are mixed such that the composition of the glass and its properties are relatively homogeneous.

As said, the product of the invention is improved over products obtainable by the methods of the prior art in that the lifetime of the composite during the intended use of cyclic loading is much higher relative to such a lifetime of a composite which is obtained by a method of manufacturing from the prior art. Alternatively one may prefer to see an advantage not as much in the extended lifetime, as in the potential to manufacture for instance teeth with much finer details or thinner layers which were previously not favourable due to fracture at a relatively early stage of the intended time of use.

Preferably, the SCG exponent n of the infrastructures of the present invention is at least 1, more preferably at least 3 and most preferably at least 5 higher than the SCG exponent n of an infrastructure using the same starting glass that is not treated.

The invention is further related to a glass infiltrated metal oxide infrastructure such as obtainable by a method according to the invention. Also glass infiltrated metal oxide infrastructures of which 1 wt % to 5 wt % of the oxygen has been replaced by nitrogen via other processes than discussed here will exhibit the superior mechanical properties, such as a high SCG exponent n.

According to another aspect of the invention the glass of the glass infiltrated metal oxide infrastructures has a coefficient of expansion comparable to a coefficient of expansion of the infrastructure. This prevents large internal stresses to be induced upon cooling down from the infiltration temperature. As a result the cyclic loading, a glass infiltrated metal oxide infrastructure may in use be subjected to, remains symmetrical i.e. is not offset by a stress which is permanently present within the composite due to a mismatch in shrinkage.

Another aspect of the invention is related to a method for avoiding or reducing stress corrosion in a glass infiltrated metal oxide infrastructure, comprising heating a glass composition comprising alumina in an amount between 12 wt % and 23 wt % and calcium oxide in an amount between 1 wt % and 26 wt %, the balance being silica, under a nitrogen-rich gas atmosphere before infiltrating the metal oxide infrastructure.

As said, the metal oxide infrastructure may instead of alumina comprise magnesium/aluminium based spinel structures and/or, a zirconium oxide and/or hydroxyapatite (HA) and/or zirconia toughened alumina. The glass which is to be infiltrated in the HA preferably comprises 50-55 wt % $SiO_2$, 20-25 wt % $B_2O_3$ 10-20 wt % $Li_2O$ and 0-6 wt % CaO, being chemically nearly compatible with HA. Composites of such a metaloxide infrastructure and an infiltrated glass may be fabricated using a melt-infiltration process at 850-950° C.

These glass/HA composites can be used for manufacturing ceramic components for biomedical applications. Test have shown that these composites have excellent mechanical properties, such as fracture strength of 76 MPa and toughness of 0.76 $MPa \cdot m^{1/2}$. These values are comparable with those of dense HA.

The nitridation treatment may in general also be carried out using a molten nitride at a temperature in a range from 1200° C. to 1600° C. for at least 8 up to 16 hours.

The present invention will now be further illustrated while referring to the following, non-limiting example. Percentages are, unless otherwise indicated, weight percentages drawn to the weight of the total composition in the description, examples and claims.

EXAMPLE 1

An alumina infrastructure was prepared by uniaxially pressing alumina powder under about 6.5 MPa in discs of 62 mm in diameter to obtain a thickness of about 5 mm. The original powder contained alumina particles of several μm in diameters. The discs were sintered for three hours in air at a temperature between 1100° C. and 1400° C.

The glass was formed by wet ball milling the following oxides

| | oxide | | | | | color |
|---|---|---|---|---|---|---|
| | $SiO_2$ | $B_2O_3$ | $Al_2O_3$ | $La_2O_3$ | $TiO_2$ | CaO | agents |
| wt % | 20 | 19 | 20 | 30 | 4 | 5 | 2 | in alcohol for 24 hours to obtain a powder mixture.

The glass was then for 8 hours kept at 1400° C. under a nitrogen gas atmosphere.

The glass was subsequently put on a topside of the alumina discs and heated for 6 hours at a temperature of about 1250° C. under a nitrogen gas atmosphere.

From the glass infiltrated metal oxide infrastructures samples beams, each with a size of 5 mm×3 mm×1 mm, were cut and ground. Each beam was then fractured using a three point bending fixture under stressing rates ranging from 0.02 MPa/s to 3.8 MPa/s.

The results are shown in FIG. 1. A straight line is drawn through the data applying the least squares method. The slope of the line equals 1/(n+1) and the SCG exponent n is determined to be 30. The n value for the glass alumina composite which has not been subjected to the heating in a nitrogen rich environment was found to be 21.

EXAMPLE 2

A commercial HA powder (Merck, Darmstadt, Germany) was used to prepare porous HA preforms as well as dense HA. The powder was first sieved using a 0.25 mm mesh to get rid of large agglomerates, followed by uniaxially pressing under 5 MPa to form tablets of nominal dimensions of 60×60×6 $mm^3$. The pressed tablets were then sintered at 1100° C. for 4 h in air.

Also dense HA tablets were sintered to nearly fully dense at 1300° C. for 6 h under the mixed atmosphere of air and water vapor obtained by passing air through a water contained coil at room temperature. The dense HA tablets were employed for the comparison of mechanical properties with infiltrated HA/glass composites.

A borosilicate glass is made through melting mixtures of oxides and carbonates in at 1250-1400° C. in air for 2-4 h, followed by quenching glass melts in water. The glass is then for 8 hours kept at 1400° C. under a nitrogen gas atmosphere. The composition of this glass is as follows:

| | oxide | | | |
|---|---|---|---|---|
| | $SiO_2$ | $B_2O_3$ | $LiO_2$ | CaO |
| wt % | 50-55 | 20-25 | 10-10 | 0-6 |

Dense HA/glass composites were fabricated by spontaneous infiltration of the HA preforms by the glass at a temperature above 850° C. during a time between 1-4 h.

The fracture strength of the composite and of the dense HA structure was measured by a three-point bending test with a span of 10 mm and a crosshead speed of 0.5 mm/min in air using specimens with nominal dimensions of 3×2×15 $mm^3$. Specimens for this test were cut from the infiltrated and sintered samples using a diamond saw, and ground using 80 grit SiC polishing papers. They were then lapped to the nominal dimensions using 320 grit SiC polishing papers. The fracture toughness was determined by the indentation strength (IS) method on beams of the same dimensions as used for the strength test. Prior to fracture, an indentation was made by a Vickers indenter using a dwell time of 30 s under a load of 19.6 N. The fracture toughness was then calculated according to the equations in Chantikul P, Anstis G R, Lawn B R, Marshall D B. *A critical evaluation of indentation techniques for measuring fracture toughness: II, strength method. J Am Ceram Soc* 1981; 64: 539-4. A total of 5-8 specimens was tested for both the strength and toughness tests. The composite has a strength value of 76 MPa and a toughness value of 0.76 $MPa \cdot m^{1/2}$.

The densely sintered HA had a strength value of 76 MPa and a toughness value of 0.77 $MPa \cdot m^{1/2}$. Therefore, it can be concluded that the fracture strength and toughness of the newly developed HA/glass composite are comparable with those of dense HA.

The leaching resistance of various glasses was roughly tested through immersing a piece of glass of ~0.5 g into 50 ml distilled water at 70° C. for up to one week. The leaching rate (L) was then determined using the following equation.

$$L = \frac{W_0 - W_t}{W_0} \times 100 \times \frac{1}{t}$$

where $W_0$ and $W_t$ are the weight of a sample before and after the leaching test and t is the leaching time in minute. The leaching rate of a commercial glass (DURAN®, Schott Glass, Mainz, Germany) was also measured using the same procedure as above for comparison. The glass has relatively good leaching resistance, where the leaching rate of the glass was determined to be $6\times10^{-5}$%/min, which is just 3 times higher than that of the window glass. It should be noted that the leaching resistance of the glass might be further improved through adding small quantity of other oxides such as $Al_2O_3$.

Various phases of the infiltrated samples were analyzed using X-ray diffractometer (XRD). Results showed that the glass is nearly chemically compatible with HA at least up to 1000° C.

The invention claimed is:

1. A method for manufacturing a composite of a porous metal oxide infrastructure and a glass infiltrated in the pores of the infrastructure, wherein the method comprises the following steps:
   providing a glass which is suitable for infiltration and compatible with the metal oxide infrastructure;
   heating the glass in a nitrogen rich gas environment; and
   infiltrating the metal oxide infrastructure with the glass.

2. Method according to claim 1, wherein the heating is carried out under a nitrogen rich gas atmosphere.

3. Method according to claim 2, wherein the heating is carried out under a nitrogen gas.

4. Method according to claim 1, wherein the heating is at a temperature in a range from 1200° C. to 1600° C.

5. Method according to claim 1, wherein the heating is carried out for at least 4 up to 16 hours.

6. Method according to claim 5, wherein the heating is carried out for at least 6 up to 10 hours.

7. Method according to claim 1, wherein the glass has a surface energy at said infrastructure which is at an infiltration temperature lower than a surface energy of the infrastructure.

8. Method according to claim 1, wherein the glass comprises metal oxides which are employed in the infrastructure wherein each metal oxide is present in a slightly less amount than at a saturation of the glass relative to that metal oxide at an infiltration temperature.

9. Method according to claim 1, wherein the metal oxide in the glass comprises aluminium oxide.

10. Method according to claim 1, wherein the glass comprises alumina in an amount between 12 wt % and 23 wt %, calcium oxide in an amount between 1 wt % and 26 wt %, the balance being silica.

11. Method according to claim 1 wherein the glass comprises up to 30 wt. % $B_2O_3$, up to 45 wt. % $La_2O_3$, up to 8 wt. % $TiO_2$ and optionally colouring agents and processing aids.

12. Method according to claim 1, wherein the metal oxide infrastructure comprises a structure which is at least one selected from the group consisting of alumina, zirconia toughened alumina, magnesium spinels, aluminium spinels and hydroxyapatite.

13. Method according to claim 12, wherein the metal oxide of the infrastructure comprises alumina in an amount between 80 wt % and 99.9 wt %.

14. Method according to claim 1, wherein the metal oxide of the infrastructure comprises zirconium oxide in an amount up to 20 wt %.

15. Method according to claim 1, wherein the metal oxide of the infrastructure comprises magnesium oxide in an amount up to 4 wt %.

16. Method according to claim 12, wherein the glass used for infiltrating hydroxyapatite comprises 20% to 30% $B_2O_3$, 10%-25% $Li_2O$, the balance being silica and 0-6 wt. % CaO.

17. Method for avoiding or reducing stress corrosion in a glass infiltrated metal oxide infrastructure, comprising heating a glass composition under a nitrogen rich gas atmosphere before infiltrating the metal oxide infrastructure.

* * * * *